United States Patent
Goldstein

(10) Patent No.: US 12,161,867 B2
(45) Date of Patent: *Dec. 10, 2024

(54) BIOMETRIC SENSOR

(71) Applicant: Intellishot Holdings Inc., Delray Beach, FL (US)

(72) Inventor: Steven Wayne Goldstein, Delray Beach, FL (US)

(73) Assignee: Intellishot Holdings Inc., Delray Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/129,876

(22) Filed: Apr. 2, 2023

(65) Prior Publication Data
US 2023/0248971 A1 Aug. 10, 2023

Related U.S. Application Data

(63) Continuation of application No. 17/407,570, filed on Aug. 20, 2021, now Pat. No. 11,642,522, which is a
(Continued)

(51) Int. Cl.
*A61N 1/36* (2006.01)
*A61B 5/0533* (2021.01)
(Continued)

(52) U.S. Cl.
CPC ........ *A61N 1/36028* (2013.01); *A61B 5/0533* (2013.01); *A61N 1/0456* (2013.01);
(Continued)

(58) Field of Classification Search
CPC ........ A61B 2562/0261; A61B 2562/08; A61B 5/0075; A61B 5/1072; A61B 5/1075;
(Continued)

(56) References Cited

U.S. PATENT DOCUMENTS

| | | | | |
|---|---|---|---|---|
| 4,804,943 A | * | 2/1989 | Soleimani | G08B 21/0213 340/539.1 |
| 5,392,029 A | * | 2/1995 | Chang | G08B 15/005 463/47.4 |

(Continued)

FOREIGN PATENT DOCUMENTS

IN 202011009171 A * 9/2021

*Primary Examiner* — Muhammad Adnan
(74) *Attorney, Agent, or Firm* — HEA Law PLLC; Darrin A. Auito

(57) ABSTRACT

An access control unit having a novel structure and arrangement, including a first layer comprising an electrostimulation contact interface, a second layer including a biometric sensor coupled to the electrostimulation contact interface, and a third layer including a microprocessor unit in communication with the electrostimulation contact interface. The second layer is sandwiched between the first layer and the third layer. The electrostimulation contact interface comprises one or more anode/cathode arrays configured to deliver neurostimulative excitations to the electrostimulation contact interface to elicit behavior modification.

19 Claims, 1 Drawing Sheet

Related U.S. Application Data continuation of application No. 17/151,573, filed on Jan. 18, 2021, now Pat. No. 11,100,737.

(60) Provisional application No. 62/963,107, filed on Jan. 19, 2020, provisional application No. 62/963,110, filed on Jan. 19, 2020.

(51) Int. Cl.
*A61N 1/04* (2006.01)
*G06F 3/041* (2006.01)
*G07C 9/00* (2020.01)

(52) U.S. Cl.
CPC ....... *A61N 1/0476* (2013.01); *A61N 1/36031* (2017.08); *A61N 1/36034* (2017.08); *G06F 3/041* (2013.01); *G07C 9/00563* (2013.01); *G06F 2203/04101* (2013.01)

(58) Field of Classification Search
CPC ....... A61B 5/441; A61B 5/489; A61B 5/6803; A61B 5/6824; G06F 21/32; G06F 21/35; G06K 9/0004; G07C 9/257; H04L 63/0861; H04W 12/06; H04W 12/61; Y04S 40/20

See application file for complete search history.

(56) References Cited

U.S. PATENT DOCUMENTS

| | | | | |
|---|---|---|---|---|
| 5,790,028 | A * | 8/1998 | Lee | A45C 13/24 340/539.1 |
| 5,801,617 | A * | 9/1998 | Langner | B60R 25/0225 340/426.31 |
| 5,916,087 | A * | 6/1999 | Owens | F41A 23/18 5/503.1 |
| 5,969,595 | A * | 10/1999 | Schipper | B60R 25/33 340/988 |
| 6,727,801 | B1 * | 4/2004 | Gervasi | G08B 15/02 340/5.3 |
| 6,727,817 | B2 * | 4/2004 | Maloney | G08B 13/2417 340/568.2 |
| RE43,415 | E * | 5/2012 | Tuttle | G08B 21/0286 340/541 |
| 8,839,796 | B2 * | 9/2014 | Reese | H05C 1/00 128/875 |
| 9,119,539 | B1 * | 9/2015 | Dotan | H04L 67/14 |
| 9,480,846 | B2 * | 11/2016 | Strother | A61N 1/3787 |
| 10,002,474 | B1 * | 6/2018 | Fernandez | G07C 9/20 |
| 10,617,188 | B1 * | 4/2020 | Hooks | G08B 21/0297 |
| 10,629,058 | B1 * | 4/2020 | Nengelken | F41C 33/041 |
| 11,100,737 | B1 * | 8/2021 | Goldstein | G06F 3/041 |
| 2003/0074039 | A1 | 4/2003 | Puskas | |
| 2003/0163709 | A1 | 8/2003 | Milgramm et al. | |
| 2003/0214418 | A1 * | 11/2003 | Hahne | F41H 13/0018 119/720 |
| 2005/0285747 | A1 * | 12/2005 | Kozlay | G08B 21/22 340/539.13 |
| 2006/0049938 | A1 | 3/2006 | Wilson | |
| 2006/0055534 | A1 | 3/2006 | Fergusson | |
| 2006/0248341 | A1 | 11/2006 | Lambert et al. | |
| 2010/0031139 | A1 | 2/2010 | Ihara | |
| 2010/0304874 | A1 * | 12/2010 | Abatemarco | H05C 1/00 239/602 |
| 2010/0311390 | A9 * | 12/2010 | Black | H04M 1/05 455/410 |
| 2011/0102137 | A1 * | 5/2011 | Schroter | A61B 5/1072 340/5.52 |
| 2012/0178065 | A1 * | 7/2012 | Naghavi | G09B 19/0092 434/236 |
| 2012/0222667 | A1 | 9/2012 | Vendramini et al. | |
| 2012/0298119 | A1 * | 11/2012 | Reese | H05C 1/00 128/869 |
| 2013/0244724 | A1 * | 9/2013 | Monti | H04M 1/0202 455/556.1 |
| 2015/0254948 | A1 | 9/2015 | Acosta et al. | |
| 2018/0122167 | A1 | 5/2018 | Maggioni | |
| 2018/0349589 | A1 | 12/2018 | Perna et al. | |
| 2019/0050618 | A1 * | 2/2019 | Khuri-Yakub | G06F 3/0436 |
| 2019/0278897 | A1 * | 9/2019 | Zhang | G06F 21/604 |
| 2019/0282152 | A1 | 9/2019 | Ouwerkerk | |
| 2019/0286806 | A1 * | 9/2019 | Robinson | H04W 12/10 |
| 2020/0003511 | A1 | 1/2020 | Deng et al. | |
| 2020/0035052 | A1 | 1/2020 | Arnold | |
| 2021/0020008 | A1 | 1/2021 | Deutsch | |
| 2021/0213286 | A1 | 7/2021 | Covalin et al. | |

\* cited by examiner

BIOMETRIC SENSOR

REFERENCES TO THE RELATED PATENT APPLICATION

The present application claims priority to and is a continuation application of pending U.S. application Ser. No. 17/407,570, filed Aug. 20, 2021, which claims priority to and is a continuation of U.S. application Ser. No. 17/151,573, filed on Jan. 18, 2021 (now U.S. Pat. No. 11,100,737), which claims benefit of U.S. Provisional Application Nos. 62/963,110 and 62/963,107, both filed on Jan. 19, 2020. The content of the above documents is incorporated herein by reference in its entirety.

TECHNICAL FIELD

The present disclosure relates to the field of biometric type sensors, namely sensors which require touch or close proximity to activate. More specifically, an access control system including a biometric type sensor coupled to an electro-stimulation contact interface on an object, the electro-stimulation contact being designed to activate in the event of an unauthorized attempt to access the object via the biometric type sensor.

BACKGROUND

A biometric sensor is a transducer that changes a biometric trait of a person into an electrical signal. Biometric traits typically include biometric fingerprint reader, nerves, iris, face, voice, etc. Fingerprint sensing and matching is a reliably and widely used technique for personal identification and verification. For example, a common approach to fingerprint identification includes scanning and storing a sample fingerprint or an image thereof. The characteristics of the sample fingerprint may then be compared to information for reference fingerprints already in a database to determine proper identification of a person, such as for verification purposes. Verification may determine access or securing of, for example, the following: computer centers, radioactive or biological danger areas, controlled experiments, information storage areas, airport maintenance and freight areas, hospital closed areas, pharmaceutical storage spaces, houses, businesses, safe deposit boxes, vaults, safes, and physical objects, such as firearms and merchandise.

One disadvantage of the existing biometric security solutions is that they do not interactively deter (fight back) an unauthorized user attempting access, rather they only validate a user's identity and permit access or egress or both.

Behavior modification (or change) refers to a modification of behavior of a mammal (including a human being) and may be realized in different forms, for example it may be used to aide in the formation of new habits or repeated behaviors (either avoided or induced), to guide someone or something into or away for an action, activity, or such at a moment in time. In this way the concept of behavior modification is inclusive of habit cessation, habit formation, or action guidance. Neurostimuli are often used to direct mammalian behavior.

However, in the context of authorizing access to restricted areas or spaces, it is difficult to direct individuals to specific locations or positions such that neurostimuli may be administered to the individual, e.g., to deter further attempts at accessing restricted area or space.

SUMMARY OF THE INVENTION

Embodiments of the present disclosure address deficiencies of the art with respect to behavior modification and provide a novel and non-obvious method and system for variable neurostimulative excitation to elicit behavior modification integrated with biometric sensors such that individuals are directed to the neurostimulative excitations.

The science of neurostimulation includes auditory, optical, electrical, olfactory, gustatory, alone or in any combination thereof. One aspect of the present disclosure focuses on electrical neurostimulation, but it is known that the techniques taught herein may be applied to one or more types of neurostimulation, alone or in combination, to elicit behavior modification. The combination of neurostimulation can be delivered in serial or parallel.

One object of the present disclosure is to provide an access control system and associated methods for reliably controlling access and interactively deterring (fighting back) unauthorized users access to the secured location and/or object. Another object is to provide a contextually aware interactive deterrent, e.g., providing the correct level and type(s) of deterrents based on a dynamic changing environment as well as time of day and location. Another object is to increase the time required for an unauthorized user to access a secured location and/or object.

This and other objects, features and advantages in accordance with the present invention are provided by an access control system comprising a sensor (e.g., biometric fingerprint sensor or other biometric type sensor which requires touch or close proximity, e.g., ¼ inch airgap, to activate), and an electrostimulation contact area coupled to the biometric type sensor, wherein the electrostimulation contact interface includes one or more anode/cathode arrays configured to deliver neurostimulative excitations to elicit behavior modification, e.g., deter attempts to access restricted area or space). This may also optionally include an integration of the underlying electronics necessary to process and power these components as well as transmit and receive information from external sources.

According to one embodiment, a sensor layer is sandwiched between an upper layer including a neurostimulation component layer and an electronics layer below. In this orientation, a user will be required to authenticate at the same location that neurostimulation may be administered.

The applications of this concept for behavior modification are far reaching, for example, the behavior modification system taught herein could be applied in the applications described below.

Embodiments of the present disclosure can be incorporated into a "virtual safe" (e.g., a safe that is created is a space within a digital domain that can be represented within any physical or virtual location), a gun handle (e.g., so that a portion of the handle "shocks" a person trying to hold the gun when that person is not authorized by the biometric type sensor to do so), an autonomous vehicle (e.g., so that the chassis of vehicle or payload "shocks" a person trying to touch the chassis or payload when that person is not authorized, e.g., access only permitted at defined destination location, etc.) or a door lock (e.g., so that a portion of the door handle "shocks" a person trying to turn the handle or push open the door when that person is not authorized by the biometric type sensor to do so) The present disclosure is not limited to the above examples. For example, the method and system described herein may apply to many other markets or domains such as animal control, crowd control, home or building security, teaching, learning to play music, enhancing the movement of a golf swing, improving running, detouring access to controlled substances etc.

According to another aspect of this embodiment, the neurostimulation can be delivered without the user making physical or direct contact with the device. For example, in the case of electro-neurostimulation, once the proximity of the user has been detected and authorization denied, the neurostimulus signal can be propagated using a high voltage discharge system capable of crossing a spark gap enabled by a Tesla coil. Tesla coils can produce output voltages from 50 Kilovolts of volts. The alternating current output is in the range typically between 50 kHz and 1 MHz.

The system may include an authentication electronics for determining whether the user is authorized for access to the object or space and countermeasure disabling electronics for disabling countermeasure electronics, such as energy source configured to deliver electrical neurostimulus to at least one of a plurality of electrostimulus end points on the object or device, when the user is authenticated for access to the object or space.

According to one embodiment, the authentication electronics can be incorporated in the sensor configured to detect placement of a first anatomical portion of a body in proximity to a surface of the object. The authentication electronics can include a biometric interface used to authenticate the user and provide access to the object or space without delivering an electrical neural stimulus to the user. The biometric interface can take the form of voice recognition, facial recognition, iris recognition, fingerprint recognition, ear print recognition, gait and cadence recognition, ECG ID recognition, or other forms of biometric identifiers including subcutaneous identifiers known as vein detection.

The authentication electronics may communicate with an authentication engine that may be part of a controller for the system. The authentication electronics may be configured to acquire and store information, e.g., palm print, fingerprint and geometry, every time a user attempts to gain access to the object. Thus, the system is configured to preserve authorized and non-authorized user attempts. During setup or other, the system learns the authorized users vein patterns, hand geometry, etc.

In use, the system, for example, can transmit all actions encountered by the authentication engine, such that an administrator of the system can receive live time coded information (e.g., video feeds, pictures, etc.). The information can be preserved locally or in the cloud, for forensic applications.

According to another embodiment, a data processing system is adapted for use with the invention. The data processing system includes an object, a power source, an energy source, a sensor operatively coupled to the object and sensing placement of a first anatomical portion of a body or anatomical portion of a target subject in proximity to a surface of the object and a multiplicity of electrostimulative end points coupled to the power source and affixed to the surface of the object. The system further includes a controller coupled to the sensor and end points. The controller includes a processor, memory and computer program instructions stored in the memory. In one embodiment the instructions are enabled upon execution by the processor to deliver electrical neural stimulus through one of the end points nearest to a location of the sensed placement, detect a characteristic of the sensed placement, and respond to the characteristic by changing a profile of the electrical neural stimulus.

Additional aspects of the disclosure will be set forth in part in the description which follows, and in part may be derived from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The following drawings illustrate examples of various components of embodiments of the invention disclosed herein and are for illustrative purposes only. Embodiments of the present invention are illustrated by way of example and not limitation in the figures of the accompanying drawings, and in which.

DETAILED DESCRIPTION

Figure 1A:
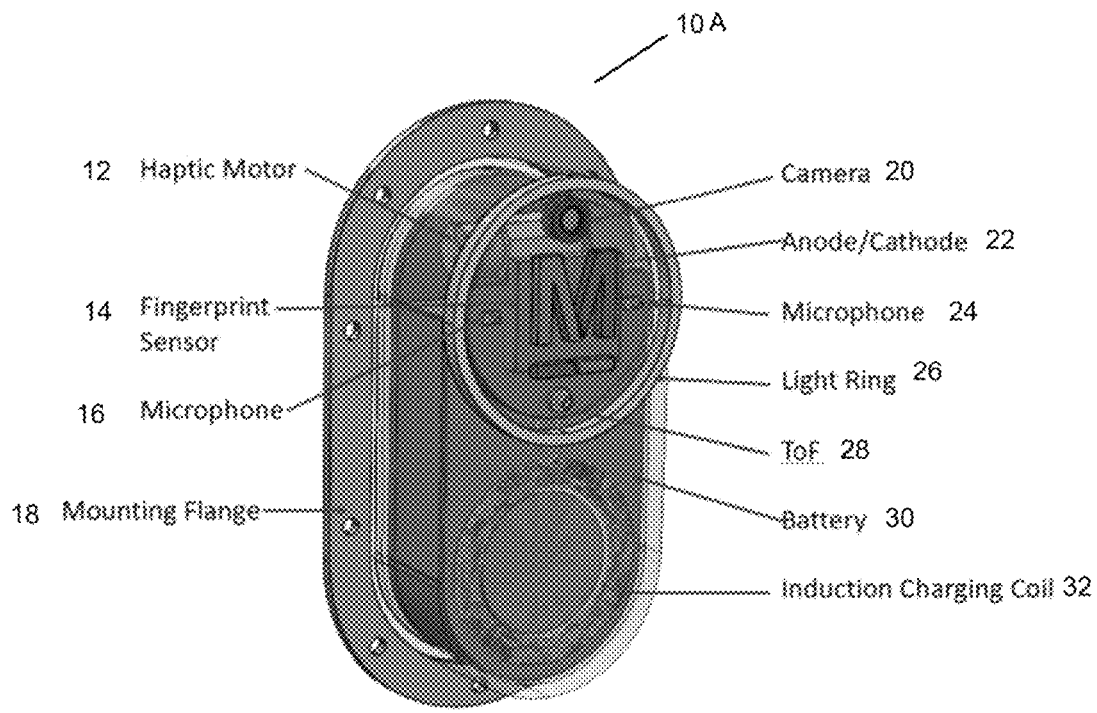
FIG. 1A illustrates a first side view (e.g., front) of one embodiment of an access control unit, e.g., integrated authentication and neurostimulation device.

The following detailed description is provided with reference to the figures. Exemplary embodiments are described to illustrate the disclosure, not to limit its scope, which is defined by the claims. Those of ordinary skill in the art will recognize a number of equivalent variations in the description that follows without departing from the scope and spirit of the disclosure.

Embodiments of the disclosure are described that provide for integrated authentication and neurostimulation for behavior modification.

In accordance with one embodiment, a proximity of a portion of the anatomy of a target subject is sensed in connection with a surface of a target object (e.g., door, door handle, jail cell, safe, locker, shipping container, computer, laptop, firearm, cellphone, piano key, golf club, baseball bat, etc.) that separates a protected space or area. The sensing of the proximity of the anatomical portion may be accomplished by several means including, but not limited to, ultrasonic, optical, acoustical, image recognition, biometric, radiofrequency, magnetic, chemical, altimeter, thermal, humidity, light, SPL (level) keyword, inductive, capacitive, resistive, inertial measurement unit, movement, rotation, force (for example by means of a strain gauge) or the sensing of current flowing in the system. Upon sensing the proximity of an anatomical portion with the surface, an identity of the target subject and a location on the surface proximate to the anatomical portion of the target subject is determined. Then, it is determined whether the target subject is authorized to access the protected space or area (e.g., inside of safe). If the target subject is authorized, then it is granted access and the system may be turned off. If the anatomical portion is not authorized, neurostimulation may be applied to a determined location for behavior modification.

According to one embodiment, an access control unit 10 (front 10a, back 10b) comprises a biometric sensor coupled to an electro-stimulation contact interface. The biometric sensor (e.g., fingerprint sensor 14) may be positioned below, either partially or entirely, the electro-stimulation contact surface. The biometric sensor may be a biometric fingerprint sensor 14 (or other biometric type sensor which requires touch or close proximity (approximately ¼ inch gap) to activate) coupled to the electro-stimulation contact area, which may include one or more additional anode/cathode arrays. The access control unit 10 may be used, for example, to activate or deactivate an area or product that is under supervision of an electronic enabled security system. Typically, for example, biometric sensors only identify and authenticate a user, thus allowing the user access or in some cases securing an area or product. However, according to this embodiment, the unit provides a contextually aware interactive deterrent (e.g., "fights back"), using a desired level and type of deterrent(s) based on a dynamic changing environment factors such as time of day, weather, and location.

According to one embodiment, the unit comprises a top layer of at least one set of an anode and cathode 22 configured to deliver electro-stimulation enabled by a High Voltage Generator operatively coupled to the anode and cathode. It may also include a Galvanic Skin Response Amplifier (GSRA) for threshold measurement of galvanic skin response (e.g., a change in the electrical resistance of the skin caused by emotional stress, measurable with a sensitive galvanometer, such as in lie-detector tests). It may also include a Time of Flight (ToF) sensor 28 to measure activity and determine proximity as well as Inertial Measurement Unit (IMU) to measure moment. It may also include an additional Super-High Voltage Generator enabled, for example, by a Tesla coil or other step-up voltage design. Also, for user feedback and touch affirmation, it can include a haptic transducer. Plus, it can include one or more of the following: computer vision, IR vision, thermal sensing, strain, RF, magnetometer, GPS, and other types of sensors used to detect the presence, speed, movements, actions, SPL levels, acoustic profiles, key word detection, and/or identification of a user and the physical location of the system and deterrents.

It is known that artificial intelligence (AI) and machine learning (ML) will be leveraged throughout the process, aided by feedback provided by one or more of the sensors incorporated into the system. According to one aspect, for example, an optimal profile is learned over time for each target subject by first identifying the subject, either biometrically or by external identification means such as but not limited to identification badge, image recognition, feature detection, voice recognition, iris recognition, chemical analysis, DNA analysis, motion analysis, weight and height, gait analysis, and the like. Thereafter, the nature of the change in profile of the electrical neurostimulus applied to the target subject is recorded in connection with the target subject. Subsequently, upon identifying the target subject, the same change in the profile of the electrical neurostimulus may be applied to the target subject at the outset upon sensing the placement to ensure that repeatable and consistent behaviors are performed to achieve the desired behavioral modification outcome.

Optionally, each of the anode-cathode pairs 22 is of a rounded shape, e.g., avoiding sharp corners likely to concentrate current during the delivery of an electrical neural stimulus.

According to another aspect, the electro-stimulation (e.g., electrical neurostimulus) can be delivered without the user making physical or direct contact with a pair of electrodes 22. Once the proximity of the user has been detected, the electrical neurostimulus signal can be propagated using a high voltage discharge system capable of crossing a spark gap enabled by a Tesla coil. Tesla coils can produce output voltages from 50 Kilovolts of volts. The alternating current output is in the range typically between 50 kHz and 1 MHz.

According to one embodiment, the unit comprises a second layer mounted underneath the top layer (e.g., described above) and the second layer comprises a biometric fingerprint sensor 14. The biometric fingerprint sensor may be an Ultrasonic Finger Print Sensor (UFPS) (see below). In effect, for example, the UFPS is designed to read a fingerprint through metal/glass or other substrates, thus the UFPS can be positioned beneath the top layer and can be "waterproofed" as it requires no direct contact on its surface with the finger, merely close proximity.

According to one embodiment, a set of anodes and cathodes 22 can be positioned on the same plane, but mapped around the interior or exterior boundary as a conventional fingerprint sensor.

According to one embodiment, the access control unit 10 comprises three layers (e.g., sandwich design): a first layer comprising an electrostimulation contact interface (described above), a second layer comprising a biometric sensor 14 (described above) and a third layer comprising one or more of the following: a microprocessor 52, memory (e.g., for forensics), a wired and wireless communication port and antenna array, an interface for additional deterrents and sensors. The deterrents and sensors may include one or more of the following: ultrasonic, optical, acoustical, image recognition 54, biometric, RF, magnetic, chemical, altimeter, thermal, humidity, light, SPL (level) keyword, inductive, capacitive, resistive, inertial measurement unit, force (for example by means of a strain gauge) or the sensing of current flowing in the system or from human oversight or capacitive, optical, chemical, water vapor (relative humidity RH) and encryption engine, a power supply, a wired and wireless recharging system, an IMU 60, at least one camera, ambient light, Co2, thermal sensor as to detect a precipitous change of temp (to circumvent someone attempting to cool the device as to put it to sleep), as well as a GSRA 58 to detect not only the users body (finger) impedance, but also water and or liquids that could be applied to the anode/cathode to circumvent unauthorized access, detection of and insulation of an external power being applied to the anode/cathode to circumvent unauthorized access and an interface to connect to motor, contacts, electrotechnical appliances.

Furthermore, the access control unit 10 may be configured to be activated or deactivated remotely and deterrents scaled. The unit could also be waterproofed and fireproofed to add further protective measures.

According to one embodiment, a system including an access control unit 10 (e.g., described above) acquires a fingerprint (one or more) of a user interacting with a defined area (e.g., user attempting to open a door by turning a door handle).

One advantage of the novel sandwich design of the access control unit 10 is that it can be integrated into an object that a user is likely to interact with, e.g., door handle, gun handle, container handle, etc. If the fingerprint is known, then the system is authenticated. If not, then, for example, the GSRA measures impedance in the first layer (e.g. at the anode and cathode) and delivers electro-stimulation to the fingers of the user as disclosed below. The delivery of energy to the finger, for example, is at the highest maximum transfer efficiency. There may be other locations that the electro-stimulation can be delivered. The system can also be designed to overtly direct a user to a specific physical location for fingerprint bio-identification and authentication, such that a LED or other visual indication(s) can deliver insights as to where the user is to touch or press. For example, an ultrasonic sensor can be used to detect the presence of a user when the user is in proximity of the object.

The system is configured to register multiple authorized (and unauthorized) users. For evert authorized user profile, various deterrents can be completed turned off or reduced in intensity further refined by time, location and environmental conditions.

The access control unit 10 described herein could be incorporated into embodiments of a virtual safe enabled with countermeasures to mitigate access of controlled devices or substances, described in U.S. application Ser. No. 16/732,049, filed Dec. 31, 2019 and claiming benefit to U.S. Prov. App. 62/787,171, filed Dec. 31, 2018. Applicant incorporates by reference U.S. application Ser. No. 16/732,049.

For example, it could be incorporated into a system and means of implementing and providing a contextually aware virtual perimeter enabled with interactive countermeasures to mitigate accessibility of an area or object and includes at least one sensor that establishes an electronic virtual border rom at least one point to define a space, digital detection electronics for detecting the presence of an individual, animal, or object encroaching the virtual border and countermeasure electronics for generating a countermeasure signal that impedes or thwarts the movement or actions of the detected individual, animal, or object. It could also include authentication electronics for determining whether the individual, animal, or object is authorized for access to the space and countermeasure disabling electronics for disabling the countermeasure electronics when the person, animal, or object is authenticated for access to the space.

For example, in some implementations and embodiments, contextually aware detection and monitoring can include Real Time Location System (RTLS) monitoring of a "virtual safe" (e.g., the safe that is created is a space within a digital domain and can be represented within any physical or virtual location) and its associated contents for a defined area (e.g., region of interest or protected space). The space can be enabled by an electronic virtual border around a single point with a predefined set of boundaries, such as geofencing or computer vision. Or, the tracking of a physical safe, weapon and its contents may utilize RF transceivers or magnetic transceivers, acoustic transceivers, or other whereas the safe (physical or virtual), weapon and its contents include internal or external sensors for determining location, speed of movement, heading, vibration, acceleration (e.g., 3D acceleration), or other information that can monitor the activity, state, identification of the safe, weapon and its contents to provide detection and contextual awareness. Accessing the control system can be accomplished mechanically with a key, combination lock, or electronically with a password or biometric interface (as described herein).

Countermeasures, for example, include impeding, obstructing, disrupting or terminating access by deterring, neutralizing, preventing or protecting. Countermeasures serve to deter the individual, either for a short period in the order of a 300-400 milliseconds or longer acting countermeasures, which can induce effects in the order of minutes or hours. Countermeasures include non-lethal or less than lethal measures, which can be delivered in a series of escalating steps or other patterns.

In one embodiment, countermeasures serve to cause the sensation of fight or flight. In one embodiment, the initial deployment phase of the countermeasures can begin as an Acoustic Startle Reflex, e.g., caused by an auditory stimulus greater than 120 decibels coupled with the fast rise time of the initial excitation of the acoustic transducer. Following the initial phase of the countermeasure, for example, the next deployment phase can begin in a sequential manner as to produce sound pressure levels of 140 dB, thereby inducing the Threshold of Pain, e.g., the sound pressure level beyond which sound becomes unbearable for a human listener, which varies only slightly with frequency.

With regards to electro-neurostimulation, the neural stimulus can be delivered through electrode end points, as described herein.

The foregoing arrangement is enabled to achieve neurostimulative behavior modification without risking unintended, adverse health risk given. For example, with regards to electrostimulation, the limit on current and duration of current delivery coupled with the counterbalancing delivery of energy within the AC electrical neural stimulus prevents lasting effects.

In one embodiment, when using a high-voltage system (KEV), the cathode and anode electrode placement can be modified whereas one of the electrodes is connected to the ground plane as the other electrode will cross the spark gap and deliver the electrostimulus through air.

Figure 1B:
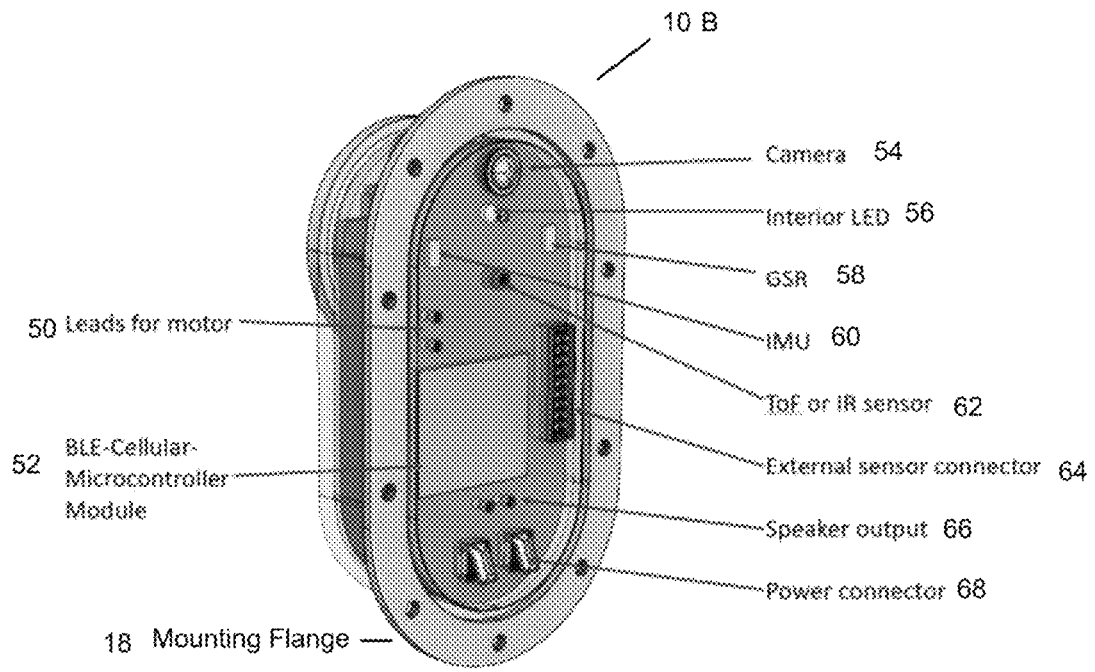
FIG. 1B illustrates a second side view (e.g., back) of one embodiment of an access control unit, e.g., integrated authentication and neurostimulation device.

FIGS. 1A and 1B illustrates a schematic of one embodiment, front and back side views respectively, of an access control unit 10 described herein, e.g., integrated authentication and neurostimulation device.

The following components are shown in FIG. 1A: haptic motor 12, fingerprint sensor 14, microphone 16, mounting flange 18, camera 20, anode/cathode 22, microphone 24, light ring 26, ToF 28, battery 30, induction charging coil 32.

The following components are shown in FIG. 1B: leads for motor 50, BLE-Cellular-Microcontroller Module 52, camera 54, interior LED 56, GSR 58, IMU 60, IR sensor 62 (or ToF sensor), external sensor connector 64, speaker output 66, and power connector 68.

The components illustrated in FIGS. 1A and 11B are illustrative and not limiting, e.g., can include one or more of components shown and could include components not shown, depending on the desired application of the unit. Further, the arrangement of these components is not limited to the example shown in the figures.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described to best explain the principles of the invention and the practical application, and to enable others of ordinary skill in the art to understand the invention for various embodiments with various modifications as are suited to the particular use contemplated.

Although this disclosure has been described in connection with specific forms and embodiments thereof, it will be appreciated that various modifications other than those discussed above may be resorted to without departing from the spirit or scope of the disclosure as defined in the claims. For example, functionally equivalent elements may be substituted for those specifically shown and described, certain features may be used independently of other features, and in certain cases, particular locations of the elements may be reversed or interposed, all without departing from the spirit or scope of the disclosure as defined in the claims.

I claim:

1. A self-contained fully intergraded access control unit comprising:
 a first layer comprising an electrostimulation contact interface;
 a second layer comprising a biometric sensor coupled to the electrostimulation contact interface; and
 a third layer comprising a microprocessor unit in communication with the electrostimulation contact interface, wherein
 the second layer is sandwiched between the first layer and the third layer of said access control unit,
 the electrostimulation contact interface comprises one or more anode-cathode arrays, and
 the one or more anode-cathode arrays are configured to deliver neurostimulative excitations to the electrostimulation contact interface when a received biometric data by the biometric sensor does not match with a prestored biometric data.

2. The self-contained fully intergraded access control unit of claim 1, wherein magnitude and type of the neurostimulative excitations delivered to the electrostimulation contact interface are based on a dynamic changing environmental factor.

3. The self-contained fully intergraded access control unit of claim 2, wherein the dynamic changing environmental factor is at least one of time of day, weather, and location.

4. The self-contained fully intergraded access control unit of claim 1, wherein
 the biometric sensor is activated when a user is in close proximity to said access control unit, and
 the one or more anode-cathode arrays are configured to deliver neurostimulative excitations to the electrostimulation contact interface depending on a result of a comparison of a received biometric data by the biometric sensor with prestored biometric data.

5. The self-contained fully intergraded access control unit of claim 4, wherein the close proximity is up to ¼ inch distance.

6. The self-contained fully intergraded access control unit of claim 5, wherein the variable neurostimulative excitations sequentially increase or decrease in magnitude when a user remains in close proximity to the access control unit.

7. The self-contained fully intergraded access control unit of claim 1, wherein the biometric sensor is a biometric fingerprint sensor.

8. The self-contained fully integrated access control unit according to claim 1, wherein the anode-cathode arrays are configured to deliver neurostimulative excitations to the electrostimulation contact interface to dissuade a non-authorized user from taking any further action to gain access via the access control unit.

9. The access control unit according to claim 1, wherein a portion of the biometric sensor is positioned below the electrostimulation contact surface.

10. The self-contained fully intergraded access control unit of claim 1, wherein the access control unit is integrated into a target object.

11. The self-contained fully intergraded access control unit of claim 10, wherein the target object is a door fixture, door handle, container handle or enclosure handle.

12. The self-contained fully intergraded access control unit of claim 10, wherein the access control unit is integrated into a target object and a magnitude of the variable neurostimulative excitations delivered increases based on an increased interaction with the target object.

13. The self-contained fully intergraded access control unit of claim 12, wherein the increased excitation is a function of amount of interaction for rotation of the target object.

14. The self-contained fully intergraded access control unit of claim 1, further comprising a high voltage generator operatively coupled to the anode-cathode arrays.

15. The self-contained fully intergraded access control unit of claim 1, wherein each of the anode-cathode arrays has a rounded shape.

16. The self-contained fully intergraded access control unit of claim 1, further comprising:
authentication electronics incorporated in the biometric sensor, wherein
the authentication electronics configured to operatively communicate with an authentication engine and to store authorized and non-authorized user interactions with the access control unit.

17. The self-contained fully intergraded access control unit of claim 16, wherein the authentication engine uses an artificial intelligence-based implementation configured to continuously learn and update an optimal profile for each user that interacts with the access control unit based in part on input received from the biometric sensor, wherein the optimal profile refers to the magnitude and type of the electrical neurostimulus delivered to the user in the event of a non-authorized user interaction with the access control unit.

18. The self-contained fully intergraded access control unit of claim 17, wherein after a subsequent interaction attempt by the same non-authorized user, the same optimal profile is applied to the user at the outset.

19. A self-contained fully integrated access control unit, comprising:
a first section on a front side of said control unit, the first section comprising an electrostimulation contact interface and a biometric sensor;
a second section on a back side of said control unit, the second section comprising a microprocessor unit in communication with the electrostimulation contact interface; and
a biometric sensor located within said control unit, the biometric sensor in communication with the microprocessor unit and the electrostimulation contact surface, wherein
the first section is connected to the second section to form said control unit,
the electrostimulation contact interface comprises one or more anode-cathode arrays, and
the one or more anode-cathode arrays are configured to deliver neurostimulative excitations to the electrostimulation contact interface when a received biometric data by the biometric sensor does not match with a prestored biometric data.

\* \* \* \* \*